United States Patent
Nakauchi et al.

(10) Patent No.: US 10,246,679 B2
(45) Date of Patent: Apr. 2, 2019

(54) METHOD FOR PRODUCING PLURIPOTENT STEM CELL HAVING IMPROVED CHIMERA FORMING ABILITY FROM PRIMED PLURIPOTENT STEM CELL, AND COMPOSITION AND COMBINATION THEREFOR

(71) Applicant: The University of Tokyo, Tokyo (JP)

(72) Inventors: Hiromitsu Nakauchi, Tokyo (JP); Hideki Masaki, Tokyo (JP); Hideyuki Murayama, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/635,331

(22) Filed: Mar. 2, 2015

(65) Prior Publication Data

US 2016/0257928 A1 Sep. 8, 2016

(51) Int. Cl.
| | |
|---|---|
| *C12N 5/00* | (2006.01) |
| *C12N 5/02* | (2006.01) |
| *C12N 15/74* | (2006.01) |
| *C12N 5/0735* | (2010.01) |
| *A01K 67/027* | (2006.01) |
| *C12N 15/85* | (2006.01) |

(52) U.S. Cl.
CPC ........ *C12N 5/0606* (2013.01); *A01K 67/0271* (2013.01); *C12N 15/85* (2013.01); *A01K 2207/12* (2013.01); *C12N 2501/235* (2013.01); *C12N 2501/415* (2013.01); *C12N 2501/58* (2013.01); *C12N 2501/60* (2013.01); *C12N 2510/00* (2013.01)

(58) Field of Classification Search
CPC .............................. C12N 5/0606; C12N 15/85
See application file for complete search history.

(56) References Cited

U.S. PATENT DOCUMENTS

| | | |
|---|---|---|
| 2005/0265980 A1 | 12/2005 | Chen |
| 2010/0009442 A1 | 1/2010 | Sasai |
| 2010/0122360 A1 | 5/2010 | Nakauchi et al. |
| 2011/0067125 A1 | 3/2011 | Nakauchi et al. |
| 2013/0211187 A1 | 8/2013 | Araki et al. |
| 2014/0338008 A1 | 11/2014 | Nakauchi et al. |
| 2016/0073616 A1 | 3/2016 | Nakauchi et al. |

FOREIGN PATENT DOCUMENTS

| | | |
|---|---|---|
| WO | 2008102602 A1 | 8/2008 |
| WO | 2009104794 A1 | 8/2009 |
| WO | 2010021390 A1 | 2/2010 |
| WO | 2012/029784 A1 | 3/2012 |
| WO | 2012/043814 A1 | 4/2012 |
| WO | 2014119627 A1 | 8/2014 |

OTHER PUBLICATIONS

Miyabayashi (2007, PNAS,104:5668-5673).*
Ten Berge (2011, Nature Cell Biology, 13:1070-1075).*
Sumi (2013, PLOSONE, 8:e63378, pp. 1-11).*
De Los Angeles (2012, Curr Opinions in Genetics and Development, 22:272-282).*
Davidson (2012, PNAS, 109:4485-4490).*
Van Amerongen (2009, Development, 136:3205-3214).*
Brons, et al., "Derivation of pluripotent epiblast stem cells from mammalian embryos," Nature, Jul. 12, 2007, vol. 448, pp. 191-195 and Method p. 1, Nature Publishing Group.
Tesar, et al., "New cell lines from mouse epiblast share defining features with human embryonic stem cells," Nature, Jul. 12, 2007, vol. 448, pp. 196-199 and Methods pp. 1-3, Nature Publishing Group.
Han, et al., "Epiblast Stem Cell Subpopulations Represent Mouse Embryos of Distinct Pregastrulation Stages," Cell, Nov. 12, 2010, vol. 143, pp. 617-627, Elsevier Inc.
Ying, et al., "The ground state of embryonic stem cell self-renewal," May 22, 2008, Nature, vol. 453, pp. 519-523 and Method p. 1, Nature Publishing Group.
Komiya et al., "Wnt signal transduction pathways," Organogenesis, vol. 4, No. 2, pp. 68-75 (2008).
Chen et al., "Small molecule-mediated disruption of Wnt-dependent signaling in tissue regeneration and cancer," Nature Chemical Biology, vol. 5, No. 2, pp. 100-107 (2009).
Huang et al., "Tankyrase inhibition stabilizes axin and antagonizes Wnt signalling," Nature, vol. 461, pp. 614-620 (2009).
Hanna et al, "Human embryonic stem cells with biological and epigenetic characteristics similar to those of mouse ESCs", PNAS, May 18, 2010, vol. 107, No. 20, pp. 9222-9227.
Japanese Office Action issued in application No. 2014-011262 dated Mar. 20, 2018.
Del Valle et al., "E-cadherin is required for the proper activation of the Lifr/Gp130 signaling pathway in mouse embryonic stem cells," Development, vol. 140, pp. 1684-1692 and supplemental pp. 1-10 (2013).
Gottardi et al., "E-Cadherin Suppresses Cellular Transformation by Inhibiting B-Catenin Signaling in an Adhesion-Independent Manner," The Journal of Cell Biology, vol. 153, pp. 1049-1059 (2001).
Guo, et al., "Epigenetic resetting of human pluripotency," Development, vol. 144, pp. 2748-2763 (2017).
Haegel, et al., "Lack of b-catenin affects mouse development at gastrulation," Development vol. 121, pp. 3529-3537 (1995).
Soncin, et al., "Abrogation of E-Cadherin-Mediated Cell-Cell Contact in Mouse Embryonic Stem Cells Results in Reversible LIF-Independent Self-Renewal," Stem Cells, vol. 27, pp. 2069-2080 (2009).

(Continued)

*Primary Examiner* — Valarie E Bertoglio
(74) *Attorney, Agent, or Firm* — Pearne & Gordon LLP (57) ABSTRACT

The present invention provides a method for putting a primed pluripotent stem cell in a less differentiated state, a method for producing a pluripotent stem cell having an improved chimera forming ability from a primed pluripotent stem cell, and a method for producing a chimeric animal by using the pluripotent stem cell obtained by any of these methods. The present invention also provides a composition containing a Wnt/β catenin signal inhibitor.

4 Claims, 6 Drawing Sheets

(56) References Cited

OTHER PUBLICATIONS

Yang, et al., "Establishment of mouse expanded potential stem cells," Nature, vol. 550, pp. 393-397 and supplemental pp. 1-16 (2017).
Han, et al., Epiblast Stem Cell Subpopulations Represent Mouse Embryos of Distinct Pregastrulation Stages, Cell, 2010, 143(4), pp. 617-627.

* cited by examiner

METHOD FOR PRODUCING PLURIPOTENT STEM CELL HAVING IMPROVED CHIMERA FORMING ABILITY FROM PRIMED PLURIPOTENT STEM CELL, AND COMPOSITION AND COMBINATION THEREFOR

BACKGROUND OF THE INVENTION

Field of the Invention

The present invention relates to a method for putting a primed pluripotent stem cell in a less differentiated state, a method for producing a pluripotent stem cell having an improved chimera forming ability from a primed pluripotent stem cell, and a method for producing a chimeric animal by using the pluripotent stem cell obtained by any of these methods. The present invention also relates to a composition containing a Wnt/β catenin signal inhibitor and a signal transducer and activator of transcription 3 (STAT3) signal activator, a combination of a STAT3 signal activator and a Wnt/β catenin signal inhibitor, and a kit containing the composition or the combination.

Description of the Related Art

A pluripotent stem cell obtained from an inner cell mass (ICM) of a blastocyst is known to have a high chimera forming ability, but a pluripotent stem cell obtained from an embryo at a later developmental stage (such as an embryo after the epiblast stage) is considered to have lost the chimera forming ability (Brons et al., Nature (2007), 448 (7150): 191-195, Tesar et al., Nature (2007), 448 (7150): 196-199, and Han et al., Cell (2010), 143: 617-627).

Pluripotent stem cells are classified into a naive pluripotent stem cell having a high chimera forming ability and a primed pluripotent stem cell having a low chimera forming ability. If a primed pluripotent stem cell can be converted to a naive pluripotent stem cell, the range of selection of cells usable as a cell to be introduced into an embryo in chimera formation can be greatly increased.

SUMMARY OF THE INVENTION

The present invention provides a method for putting a primed pluripotent stem cell in a less differentiated state, a method for producing a pluripotent stem cell having an improved chimera forming ability from a primed pluripotent stem cell, and a method for producing a chimeric animal by using the pluripotent stem cell obtained by any of these methods. The present invention also provides a composition containing a Wnt/β catenin signal inhibitor, a combination of a STAT3 signal activator and a Wnt/β catenin signal inhibitor, and a kit containing the composition or the combination.

The present inventors have found that when a Wnt/β catenin signal is inhibited, a primed pluripotent stem cell is put in a less differentiated state, more specifically, is improved in its chimera forming ability, and furthermore, is efficiently converted to a naive pluripotent stem cell. Besides, the present inventors have found that when a STAT3 signal is activated in combination with inhibition of a Wnt/β catenin signal, a primed pluripotent stem cell is more effectively put in a less differentiated state, more specifically, is improved in its chimera forming ability, and furthermore, is extremely efficiently converted to a naive pluripotent stem cell. The present invention is based on these findings.

Specifically, the present invention provides the following:
(1) A method for putting a primed pluripotent stem cell in a less differentiated state, comprising placing a primed pluripotent stem cell in a state where a Wnt/β catenin signal is inhibited and a signal transducer and activator of transcription 3 (STAT3) signal is activated.
(2) The method according to (1) above, for improving a chimera forming ability of the primed pluripotent stem cell.
(3) A method for producing a pluripotent stem cell having an improved chimera forming ability from a primed pluripotent stem cell, comprising placing a primed pluripotent stem cell in a state where a Wnt/β catenin signal is inhibited and a signal transducer and activator of transcription 3 (STAT3) signal is activated.
(4) A method for producing a chimeric animal, comprising introducing the pluripotent stem cell produced by the method according to (3) above into an embryo of a mammal.
(5) A composition for use in reversing a primed pluripotent stem cell to a naive pluripotent stem cell, comprising a Wnt/β catenin signal inhibitor and a signal transducer and activator of transcription 3 (STAT3) signal activator.
(6) A combination of a signal transducer and activator of transcription 3 (STAT3) signal activator and a Wnt/β catenin signal inhibitor.
(7) The combination according to (6) above, for use in putting a primed pluripotent stem cell in a less differentiated state.
(8) The combination according to (6) or (7) above, for use in improving a chimera forming ability of a primed pluripotent stem cell.
(9) A kit comprising the composition according to (5) above or the combination according to (6) above, for use in putting a primed pluripotent stem cell in a less differentiated state or for improving a chimera forming ability of a primed pluripotent stem cell.
(10) The kit according to (9) above, further comprising a tool for fractionating a CD31 positive cell.
(11) A method for improving a chimera forming ability of a primed pluripotent stem cell, comprising introducing E-cadherin into a primed pluripotent stem cell.
(12) A method for producing a pluripotent stem cell having an improved chimera forming ability from a primed pluripotent stem cell, comprising introducing E-cadherin into a primed pluripotent stem cell.

According to the present invention, a primed pluripotent stem cell can be extremely efficiently put in a less differentiated state, can be improved in its chimera forming ability, and/or can be converted to a naive pluripotent stem cell.

BRIEF DESCRIPTION OF THE DRAWINGS

FIG. 3 is a diagram illustrating that the expression of CD31 (Pecam-1) is remarkably increased in an EpiSC by a combination of forced expression of E-cadherin and activation of STAT3, in which (A) is a diagram illustrating that the expression of CD31 (Pecam-1) is remarkably increased in the EpiSC by a combination of the forced expression of E-cadherin and LIF stimulation, (B) is a diagram illustrating a proportion of a CD31 (Pecam-1) positive cell in EpiSCs treated by either of or a combination of the forced expression of E-cadherin and the LIF stimulation, (C) is a diagram illustrating a starting time of the expression of CD31 (Pecam-1), and (D) and (E) are diagrams illustrating that an EpiSC obtained by the combination of the forced expression of E-cadherin and the LIF stimulation makes a contribution to chimerism;

FIG. 4 illustrates that use of IWP-2 and XAV939 as Wnt/β catenin signal inhibitor results in reversion, in which (A) is a diagram illustrating that IWP-2 and XAV939 work as an inhibitor of a Wnt/β catenin signal, (B) is a diagram of a processing scheme for an EpiSC, (C) is a diagram illustrating that an EpiSC forms a naive pluripotent stem cell-like colony through a treatment with a combination of LIF and IWP-2, (D) is a graph of a proportion of the naive pluripotent stem cell colony (sometimes referred to as the naive-like colony), (E) is a diagram of an expression intensity of CD31 (Pecam-1) obtained after the treatment, (F) is a graph of a proportion of the CD31 (Pecam-1) positive cell, (G) and (H) are an optical micrograph and a fluorescence micrograph, respectively, illustrating that the obtained naive-like colony is derived from an EpiSC, and (I) is a photograph of the coat color of an obtained chimeric animal;

DETAILED DESCRIPTION OF THE PREFERRED EMBODIMENTS

In the present invention, a "primed pluripotent stem cell" means a primed pluripotent stem cell such as a primed ES cell or iPS cell. Examples of the "pluripotent stem cell" according to the present invention include, but not especially limited to, pluripotent stem cells of mammals such Primates such as a human and a monkey, and a pig, a bovine, an ovine and a goat. A primed pluripotent stem cell used in the present invention is, for example, an epiblast stem cell (EpiSC) of a mammal. A primed pluripotent stem cell used in the present invention is, for example, a human primed embryonic stem cell (ES cell) or a human primed induced pluripotent stem cell (iPS cell). The chimera forming ability of a primed pluripotent stem cell is inferior to that of a naive pluripotent stem cell.

The present inventors have found that when a Wnt/β catenin signal is inhibited in a primed pluripotent stem cell, the primed pluripotent stem cell is converted to a less differentiated state, more specifically, is improved in its chimera forming ability, and furthermore specifically, is converted to a naive pluripotent stem cell. Besides, the present inventors have found that when a signal transducer and activator of transcription 3 (STAT3) signal is activated and its Wnt/β catenin signal is inhibited in a primed pluripotent stem cell, the primed pluripotent stem cell is extremely efficiently reversed to a less differentiated state, more specifically, is improved in its chimera forming ability, and furthermore specifically, is converted to a naive pluripotent stem cell.

According to the present invention, a primed pluripotent stem cell may be changed into a cell in which a Wnt/β catenin signal is inhibited and a signal transducer and activator of transcription 3 (STAT3) signal is activated. Therefore, it would be easily understood that, according to the present invention, a primed pluripotent stem cell in which the Wnt/β catenin signal has been inhibited can exhibit the equivalent effect of the present invention merely by activating the STAT3 signal, and that a primed pluripotent stem cell in which the STAT3 signal has been already activated can exhibit the equivalent effect of the present invention merely by inhibiting the Wnt/β catenin signal. The inhibition of the Wnt/β catenin signal can be confirmed on the basis of degradation of β-catenin or the abundance of β-catenin in a nucleus. The activation of the STAT3 signal can be confirmed, for example, on the basis of the presence of phosphorylated STAT3. The inhibition of the Wnt/β catenin signal may be carried out as described below. The activation of the STAT3 signal may be carried out as described below. The inhibition of the Wnt/β catenin signal and the activation of the STAT3 signal may be properties of a primed pluripotent stem cell.

A method for activating the STAT3 signal will now be described. The STAT3 signal is considered to be activated by a protein of the IL-6 family via gp130 (namely, CD130) and a receptor associated with gp130. Accordingly, the STAT3 signal can be activated by bringing, for example, a protein of the IL-6 family and/or a gp130 agonist into contact with the cell. Examples of the protein of the IL-6 family include a leukocyte migration inhibition factor (LIF), oncostatin M (OSM), a ciliary neurotrophic factor (CNTF), and IL-11, all of which can be used in the present invention.

A method for inhibiting the Wnt/β catenin signal will now be described. When the Wnt/β catenin signal is activated, the nuclear translocation of β catenin is accelerated. The inhibition of the Wnt/β catenin signal can be achieved by inhibiting, for example, the nuclear translocation of β catenin. The inhibition of the nuclear translocation of β catenin can be achieved by accelerating degradation of β catenin in the cytoplasm. Accordingly, the inhibition of the Wnt/β catenin signal can be carried out by, for example, accelerating the degradation of β catenin in the cytoplasm and/or inhibiting the nuclear translocation of β catenin.

In order to inhibit the nuclear translocation of β catenin, the cell can be treated with a β catenin nuclear translocation inhibitor. An example of the β catenin nuclear translocation inhibitor is IWP-2. IWP-2 is also designated as N-(6-methyl-2-benzothiazolyl)-2-[(3,4,6,7-tetrahydro-4-oxo-3-phenylthieno[3,2-d]pyrimidine-2-yl)thio]-acetamide, and is presumed to inhibit the nuclear translocation of β catenin by inhibiting a protein designated as Porcupin. Any person skilled in the art can appropriately inhibit the nuclear translocation of β catenin by using a known β catenin nuclear translocation inhibitor.

In order to accelerate the degradation of β catenin in the cytoplasm, the cell can be treated with a β catenin degradation accelerator. An example of the β catenin degradation accelerator is XAV939. XAV939 is also designated as 3,5,7,8-tetrahydro-2-[4-(trifluoromethyl)phenyl]-4H-thiopyrano[4,3-d]pyrimidine-4-one, and is presumed to accelerate the degradation of a β catenin-binding protein by binding to a protein designated as Axin. Any person skilled in the art can appropriately inhibit the nuclear translocation of β catenin by using a known β catenin degradation accelerator.

In addition, the inhibition of the Wnt/β catenin signal can be appropriately carried out by using a molecule known as a Wnt/β catenin signal inhibitor. Any person skilled in the art can appropriately inhibit the nuclear translocation of β catenin by using a known Wnt/β catenin signal inhibitor.

In a primed pluripotent stem cell, when the Wnt/β catenin signal is inhibited, the expression of Pecam1 (namely, CD31) known as a marker for a naive pluripotent stem cell is increased, the chimera forming ability of the cell is improved, and the gene expression of the cell becomes close to the gene expression profile of a naive pluripotent stem cell. This revealed that when the Wnt/β catenin signal is inhibited in a primed pluripotent stem cell, the reversion of the primed pluripotent stem cell to a naive pluripotent stem cell occurs.

In a primed pluripotent stem cell, when the STAT3 signal is activated and its Wnt/β catenin signal is inhibited, the expression of PECAM-1 (namely, CD31) known as a marker for a naive pluripotent stem cell is increased, the chimera forming ability of the cell is improved, and the gene expression of the cell becomes close to the gene expression profile of a naive pluripotent stem cell.

This revealed that when the STAT3 signal is activated and its Wnt/β catenin signal is inhibited in a primed pluripotent stem cell, the reversion of the primed pluripotent stem cell to a naive pluripotent stem cell occurs. In addition, the effect was more remarkable as compared with that attained by merely inhibiting the Wnt/β catenin signal.

Accordingly, one aspect of the present invention provides a method for putting a primed pluripotent stem cell in a less differentiated state, a method for improving the chimera forming ability of a primed pluripotent stem cell, and a method for producing a pluripotent stem cell having an improved chimera forming ability (specifically, a naive pluripotent stem cell) from a primed pluripotent stem cell, by inhibiting the Wnt/β catenin signal in the primed pluripotent stem cell. Besides, a more preferable aspect of the present invention provides a method for putting a primed pluripotent stem cell in a less differentiated state, a method for improving the chimera forming ability of a primed pluripotent stem cell, and a method for producing a pluripotent stem cell having an improved chimera forming ability (specifically, a naive pluripotent stem cell) from a primed pluripotent stem cell, by activating the STAT3 signal is activated and inhibiting its Wnt/β catenin signal in the primed pluripotent stem cell.

Furthermore, according to the present invention, a primed pluripotent stem cell in which a Wnt/β catenin signal is inhibited highly efficiently makes a contribution to a chimeric animal. Accordingly, the present invention provides a method for producing a chimeric animal including: inhibiting a Wnt/β catenin signal in a primed pluripotent stem cell of a mammal; and introducing the resultant pluripotent stem cell into an embryo of a mammal. Moreover, according to the present invention, a primed pluripotent stem cell in which a STAT3 signal is activated and its Wnt/β catenin signal is inhibited highly efficiently makes a contribution to a chimeric animal. Accordingly, a preferred aspect of the present invention provides a method for producing a chimeric animal comprising: activating a signal transducer and activator of transcription 3 (STAT3) signal and inhibiting a Wnt/β catenin signal in a primed pluripotent stem cell of a mammal; and introducing the resultant pluripotent stem cell into an embryo of a mammal.

Besides, the present invention provides a composition for use in putting a primed pluripotent stem cell in a less differentiated state, for use in improving the chimera forming ability of a primed pluripotent stem cell, or for use in converting a primed pluripotent stem cell to a naive pluripotent stem cell. The composition of the present invention contains at least a Wnt/β catenin signal inhibitor. The composition of the present invention more preferably further contains a STAT3 signal activator. The Wnt/β catenin signal inhibitor used in the present invention may have a function to activate a STAT3 signal.

When E-cadherin was introduced into a primed pluripotent stem cell, its chimera forming ability was improved. Accordingly, the present invention provides a method for improving the chimera forming ability of a primed pluripotent stem cell comprising introducing E-cadherin into a primed pluripotent stem cell. The present invention also provides a composition that contains means for introducing E-cadherin (such as an E-cadherin expression vector or an E-cadherin protein) for use in improving the chimera forming ability of a primed pluripotent stem cell. The method of the present invention may further include activating a STAT3 signal. The present invention further provides a combination of a tool for introducing E-cadherin and the composition of the present invention. The combination of the present invention can be used for improving the chimera forming ability of a primed pluripotent stem cell. The combination of the present invention can be also used for converting a primed pluripotent stem cell to a naive pluripotent stem cell.

Furthermore, the present invention provides: a combination of a STAT3 signal activator and a Wnt/β catenin signal inhibitor for use in putting a primed pluripotent stem cell in a less differentiated state; a combination of a STAT3 signal activator and a Wnt/β catenin signal inhibitor for use in improving the chimera forming ability of a primed pluripotent stem cell; and a combination of a STAT3 signal activator and a Wnt/β catenin signal inhibitor for use in converting a primed pluripotent stem cell to a naive pluripotent stem cell.

The combination of the present invention may be contained in a composition as a mixture. Accordingly, the present invention provides a composition containing the combination of the present invention. The combination of the present invention may be provided in separate forms. The composition of the present invention can be used for putting a primed pluripotent stem cell in a less differentiated state, for improving the chimera forming ability of a primed pluripotent stem cell and/or for reversing a primed pluripotent stem cell to a naive pluripotent stem cell.

The present invention further provides a kit or a reagent for use in putting a primed pluripotent stem cell in a less differentiated state, a kit or a reagent for use in improving the chimera forming ability of a primed pluripotent stem cell, or a kit or a regent for use in reversing a primed pluripotent stem cell to a naive pluripotent stem cell, all of which comprise the combination of the present invention. To the kit or the reagent, an instruction describing a method for applying the combination to a cell may be attached. The kit of the present invention may further comprise means for fractioning a CD31 positive cell (for example, an anti-CD31 antibody such as a fluorescent labeled antibody to be used for sorting).

The present invention provides, as described above, a method for producing a chimeric animal comprising: obtaining a pluripotent stem cell having an improved chimera forming ability by the method of the present invention; and introducing the obtained pluripotent stem cell into an embryo of a mammal. The method of the present invention may further comprise developing the embryo into which the cell has been introduced in a womb of a non-human surrogate parent animal to obtain a fetus or an offspring. The production of a chimeric mammal usually includes introducing a cell having a chimera forming ability, such as an ES cell of a mammal, into an embryo of a mammal, transplanting the obtained embryo into the uterus of a surrogate parent animal, and obtaining a chimeric offspring from the surrogate parent animal. In the present invention, the non-human surrogate parent animal can be an animal of the same species as the embryo for introducing the cell.

In the production of a genetically modified animal, a pluripotent stem cell having a chimera forming ability is required, and the present invention provides a pluripotent stem cell having a high chimera forming ability. Accordingly, the present invention provides a method for producing, for example, a non-human genetically modified animal comprising: (i) modifying the gene of a primed pluripotent stem cell of a non-human animal; (ii) inhibiting a Wnt/β catenin signal of the cell resulting from (i) above; and (iii) introducing the cell resulting from (ii) above into an embryo of a non-human animal. A preferable aspect of the present invention provides a method for producing, for example, a non-human genetically modified animal comprising: (i) modifying the gene of a primed pluripotent stem cell of a non-human animal; (ii) activating a signal transducer and activator of transcription 3 (STAT3) signal and inhibiting its Wnt/β catenin signal in the cell resulting from (i) above; and (iii) introducing the cell resulting from (ii) above into an embryo of a non-human animal.

As a method for producing a genetically modified animal, for example, a method for producing a genetically modified animal such as a knockout mouse or a transgenic mouse is known. In the production of a genetically modified animal, a genetically modified pluripotent stem cell (such as a genetically modified ES cell) is introduced into a cleavage cavity at the blastocyst stage and the resultant cell is transplanted into the uterus of a surrogate mother to obtain a chimeric animal as an offspring. In the case where a knockout animal is to be obtained, the chimeric animal thus obtained is mated with a wild-type animal, so that an offspring heterozygously having a genome further genetically modified from that of the chimeric animal can be obtained, or heterozygous offsprings thus obtained are further mated with each other, so that an offspring homozygously having the genetically modified genome can be obtained.

By employing the method of the present invention, a chimeric animal can be produced by genetically modifying a primed pluripotent stem cell, introducing the thus obtained genetically modified cell into an embryo (an embryo at the eight-cell stage, the morula stage or the blastocyst stage) of a non-human animal (for example, a non-human mammal excluding rodents, or a vertebrate such as a bird), and transplanting the resultant embryo into the uterus of a surrogate mother. In a chimeric animal, an introduced primed pluripotent stem cell makes a contribution to the germ line, and therefore, according to the present invention, a genetically modified animal can be obtained by using a primed pluripotent stem cell as a cell to be introduced into an embryo in a mammal excluding rodents. In the production of a genetically modified animal, a cell to be introduced and an embryo are preferably derived from the same species. In the obtained genetically modified cell, a signal transducer and activator of transcription 3 (STAT3) signal can be activated and/or its Wnt/β catenin signal can be inhibited before and/or after being introduced into the embryo.

A cell obtained by the method of the present invention can be used for regeneration of an organ by utilizing blastocyst complementation (see WO2008/102602 and WO2010/021390, which are incorporated herein by reference). In these methods, a blastocyst and a cell to be introduced into an embryo may be derived from the same species or different species. The present inventors have confirmed that a chimeric animal can be obtained by introducing a marmoset iPS cell into a mouse blastocyst. Besides, a cell obtained by the method of the present invention can be used in a method for growing, to a reproductive age, an animal homozygously having a causal gene for an organ or body part defect difficult or impossible to survive by employing the blastocyst complementation (see WO2009/104794, which is incorporated herein by reference). When this method is employed, an offspring homozygously having a causal gene for an organ or body part defect difficult or impossible to survive in the next generation can be obtained, theoretically with a probability of 100%, by mating non-human animals (such as knockout non-human mammals) both homozygously having the causal gene for the organ or body part defect difficult or impossible to survive. Accordingly, by employing this method, a mammal (a founder mammal) homozygously having a causal gene for an organ or body part defect difficult or impossible to survive can be obtained. In this method, a blastocyst and a cell to be introduced into an embryo are preferably derived from the same species.

In the present invention, the term "organ" means parts constituting a viscus of an animal. Examples of the organ include, but not especially limited to, a heart, a lung, a kidney, a pancreas, a thymus, a spleen, a liver, a cerebellum, a small intestine, a colon, and a urinary bladder, and the organ can be a pancreas, a kidney or a thymus.

In the present invention, the term "body part" means any part of a body. Examples of the body part include a blood vessel, a blood, a lymphocyte, a bone and hair, and the body part can be a lymphocyte or hair. Herein, a tissue is also regarded as a body part.

In the present invention, the phrase "a cell of an animal that is a different individual from the non-human animal" means a cell that can complement an abnormality or a defect of an embryo of the non-human animal, and examples include a wild-type cell and a cell expressing a fluorescent protein or the like.

Furthermore, according to the present invention, a chimeric animal could be produced with an extremely high probability by fractioning a CD31 positive cell from a primed pluripotent stem cell in which a Wnt/β catenin signal was inhibited, and introducing the thus obtained CD31 positive cell into an embryo. Besides, according to the present invention, a chimeric animal could be produced with an extremely high probability by fractioning a CD31 positive cell from a primed pluripotent stem cell in which a STAT3 signal was activated and its Wnt/β catenin signal was inhibited, and introducing the thus obtained CD31 positive cell into an embryo. In other words, there are a large number of pluripotent stem cells having a high chimera forming ability in the CD31 positive fraction. Accordingly, any of the methods of the present invention may further comprise fractioning (selecting) a CD31 positive cell from primed pluripotent stem cells in which a Wnt/β catenin signal is inhibited, and more preferably, from primed pluripotent stem cells in which a STAT3 signal is activated and its Wnt/β catenin signal is inhibited.

EXAMPLES

Example 1: Preparation of Epiblast Stem Cell

In this example, a mouse epiblast stem cell was prepared.

Epiblast stem cells (EpiSCs) used in Examples were cells of two EpiSC lines respectively derived from BDF1 and EB3DR. The EpiSC derived from BDF1 (BDF1-EpiSC) was established from an epiblast embryo of the first filial generation (F1) obtained by mating C57BL/6 and DBA2 mice, that is, strains of mice. Besides, the EpiSC derived from EB3DR (EB3DR-EpiSC) is derived from an EB3DR-ES cell, and is an EpiSC having a DsRed-T4 gene controllably linked to a CAG expression unit. An EB3DR-derived mouse ES cell line was provided from Dr. Hitoshi Niwa (Riken Center for Developmental Biology). After establishing an EpiSC from a chimeric epiblast embryo produced by transplanting an EB3DR cell into a mouse embryo, a DsRed expressing cell was isolated by using an FACS. Both the EpiSC lines were prepared by a method described in Tesar et al., Nature (2007), 448(7150): 196-199. Specifically, a cell obtained by cutting an epiblast of a mouse was dissociated with a trypsin/EDTA solution and then seeded in a mouse embryonic fibroblast (MEF) coated plate, and subsequently, the thus grown colony was cloned to establish the EpiSC line.

The obtained EpiSC was kept in Knockout D-MEM medium supplemented with 15% Knockout serum replacement, 1% non-essential amino acid, 2 mM Glutamax or L-glutamine, 0.1 mM 2-mercaptoethanol (manufactured by Life Technologies Corporation), and a basic fibroblast growth factor (bFGF) (manufactured by PeproTech). The EpiSC was subcultured every three to five days before attaining a completely confluent state.

Example 2: Reversion of Pluripotent Stem Cell by Forced Expression of E-Cadherin In this example, E-cadherin was forcedly expressed in a primed pluripotent stem cell, so as to analyze the properties of the resultant pluripotent stem cell.

Example 2-1: Preparation of Primed Pluripotent Stem Cell in which E-Cadherin Gene is Introduced As a primed pluripotent stem cell, a BDF1-EpiSC was used. An E-cadherin gene (Cdh1, Genbank Accession No. BC098501) was introduced into the cell by using a Tet-on all-in-one inducible lentiviral vector (AiLV; Yamaguchi et al., PLOS ONE, 2012). Specifically, the Tet-on AiLV was constructed by using a tetracycline (tet) response element and a reverse tet transactivator (rtTA). In this system, E-cadherin can be expressed in a cell by adding tetracycline or its derivative, doxycycline. Incidentally, in order to distinguish a cell integrated with the virus from a cell not integrated with the virus, in this Tet-on AiLV, an EGFP was expressibly introduced into the rtTA driven by a human ubiquitin C (Ubc) promoter.

Thereafter, the BDF1-EpiSC to which the gene had been introduced was fractionated by using the fluorescence intensity of the EGFP as an index. The fractionation was carried out by using MoFlo (manufactured by Beckman Coulter, Inc.) or Aria (manufactured by Becton Dickinson). The thus obtained BDF1-EpiSC is hereinafter designated as BDF1-EpiSC-TRE-Cdh1.

As a control, BDF1-EpiSC to which the EGFP was introduced was used. The BDF1-EpiSC to which the EGFP was introduced was obtained by infecting the BDF1-EpiSC with a lentiviral vector into which the EGFP gene was introduced and thus expressible under a CAG promoter. The BDF1-EpiSC to which the gene had been introduced was fractionated by the same method as described above by using the fluorescence of the EGFP as an index. The thus obtained BDF1-EpiSC is hereinafter designated as BDF1-EpiSC-GFP.

Hereinafter, the EGFP is sometimes simply referred to as GFP.

Example 2-2: Evaluation of Reversion of Primed Pluripotent Stem Cell

Next, E-cadherin was forcedly expressed in the obtained cells to evaluate the reversion.

First, the BDF1-EpiSC-TRE-Cdh1 and the BDF1-EpiSC-GFP obtained in Example 2-2 were cultured for 4 days in a usual medium (Dox(−)) or a medium supplemented with 10 μg/mL of doxycycline (Dox(+)). Thereafter, the cells were completely dissociated with trypsin/EDTA (manufactured by Life Technologies Corporation), and then were stained with a fluorescent labeled antibody (APC labeled anti-mouse CD31-APC antibody) against CD31 (Pecam1) to be analyzed by using a FACS CANTO (manufactured by Becton Dickinson). The CD31 (Pecam1) is a naive pluripotent stem cell marker expressed in a mouse ES cell but not expressed in an EpiSC.

Figure 1:
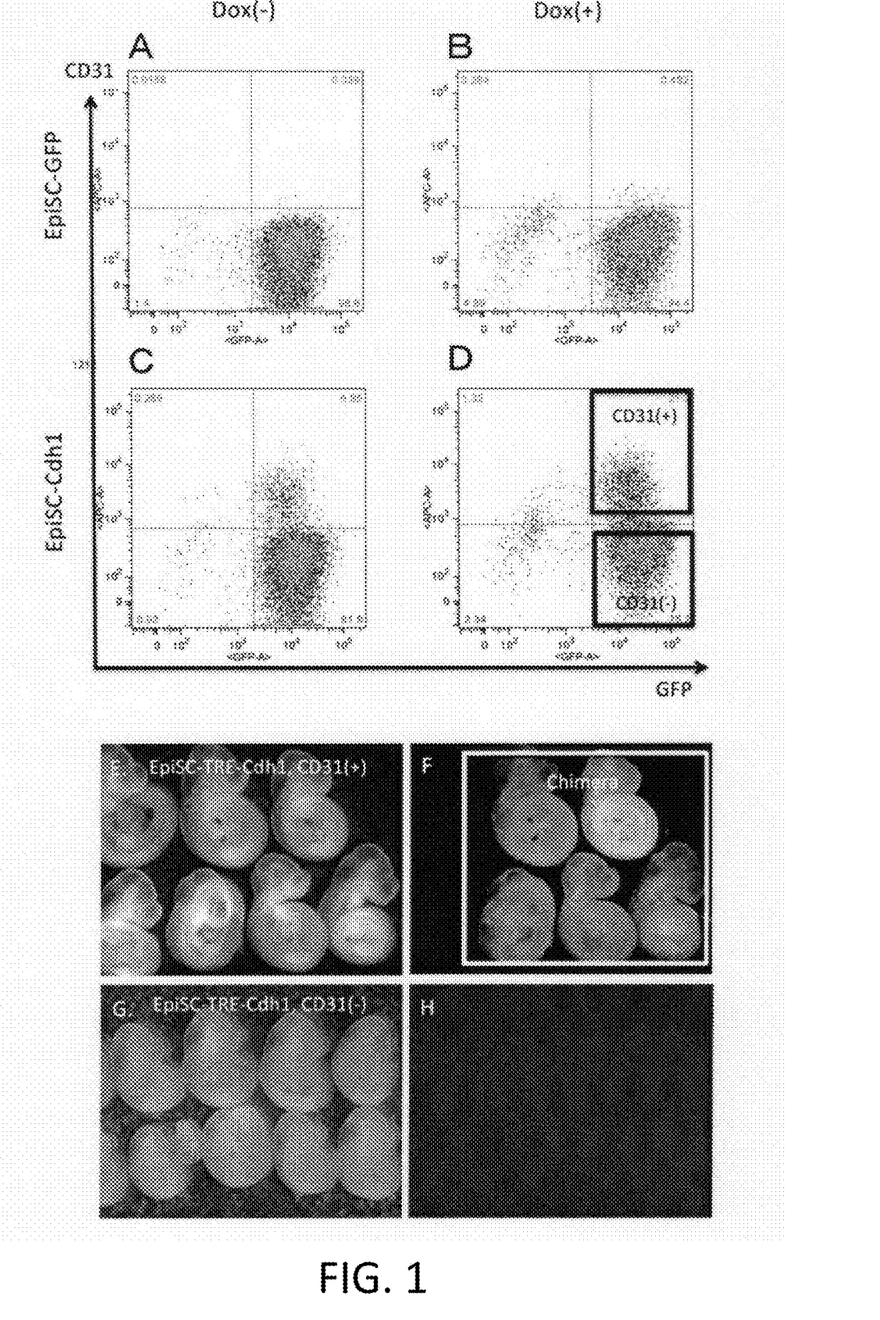
FIG. 1 illustrates that a mouse epiblast stem cell (EpiSC) is improved in its chimera forming ability and is converted to a naive pluripotent stem cell by forced expression of E-cadherin, in which (A)-(D) is a diagram illustrating the expression of CD31 (Pecam-1) in an EpiSC where E-cadherin is forcedly expressed, (E)-(H) is a diagram illustrating that the EpiSC where E-cadherin is forcedly expressed has a chimera forming ability.

As a result, substantially no CD31 positive cell was observed in the BDF1-EpiSC-GFP even under the condition of Dox(+), but a CD31 positive cell population appeared in the BDF1-EpiSC-TRE-Cdh1 under the condition of Dox(+) (see FIGS. 1, (A)-(D), and FIGS. 1, (B) and (D) in particular). This revealed that a primed pluripotent stem cell is changed into a CD31 positive cell when E-cadherin is forcedly expressed.

Next, the BDF1-EpiSC-TRE-Cdh1 (corresponding to FIG. 1, (D)) in which E-cadherin was forcedly expressed was sorted to obtain a CD31 positive cell (CD31(+)) and a CD31 negative cell (CD31(−)), and the chimera forming ability of the respective cells was verified.

First, an embryo of a BDF1 or ICR mouse was cultured in Medium 2 (manufactured by Millipore Corporation) to the eight-cell stage or morula stage. The resultant embryo was transferred to KSOM medium (manufactured by Millipore Corporation) and cultured therein for 24 hours to the blastocyst stage, and thus, a blastocyst of the mouse was obtained.

Next, into the thus obtained blastocyst, each of the CD31 positive cell and the CD31 negative cell obtained by sorting was introduced. Specifically, a zona pellucida was perforated under a microscope by using a piezoelectric micromanipulator, and a chimeric embryo was produced by injecting approximately 10 EpiSCs into a space below the zona pellucida in each embryo. Thereafter, the embryo was transplanted into the uterus of a pseudopregnant ICR recipient female mouse. Seven days after the transplantation, the chimeric embryo was excised from the recipient at a developmental stage corresponding to 9.5 days after pregnancy. The excised embryo was observed with a fluorescence microscope (manufactured by Leica).

Figure 2:
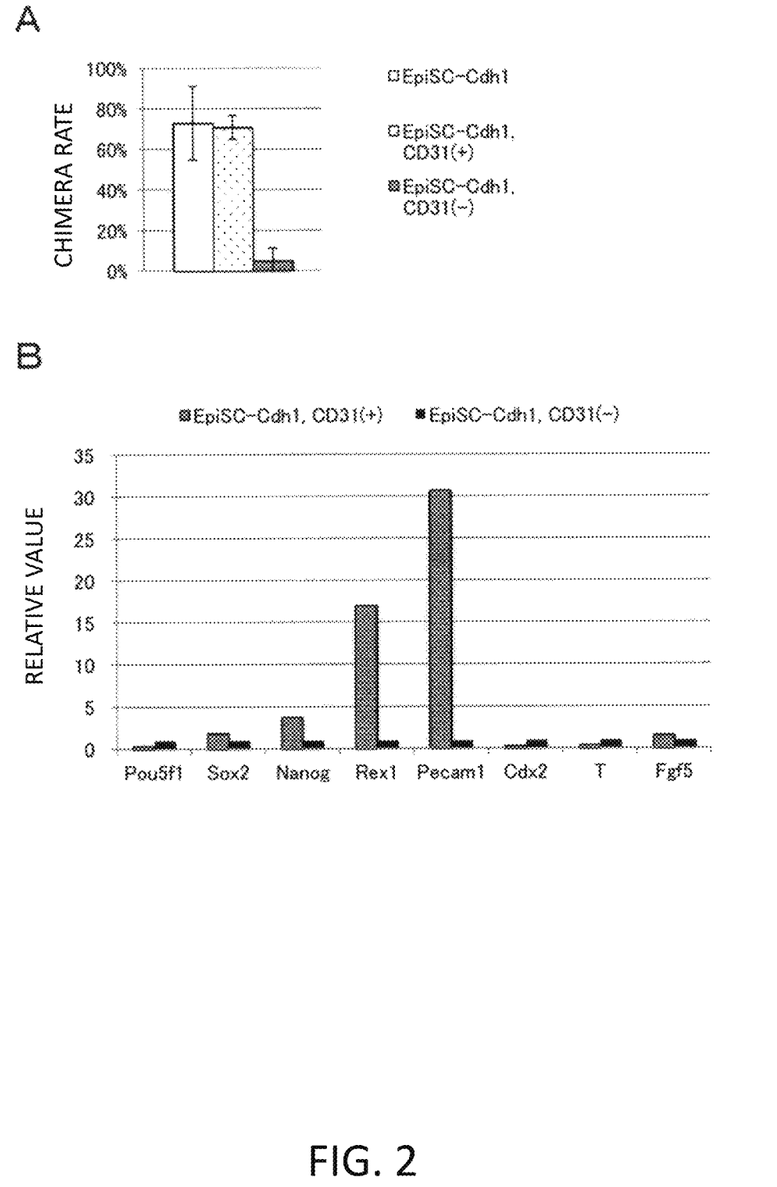
FIG. 2 illustrates that chimera forming ability is improved by forced expression of E-cadherin, in which (A) is a diagram illustrating that cells having a chimera forming ability are present in CD31 positive cells, and (B) is a diagram of a gene expression profile of an EpiSC in which E-cadherin is forcedly expressed.

As a result, an embryo expressing GFP was observed at a high frequency in the CD31 positive cell (CD31(+)) while no GFP signal was observed in the CD31 negative cell (CD31 (−)) (see FIGS. 1, (E)-(F) and (G)-(H)). This revealed that a primed pluripotent stem cell in which CD31 is expressed by introducing E-cadherin is improved in its chimera forming ability. On the other hand, also when the BDF1-EpiSC-TRE-Cdh1 in which E-cadherin was forcedly expressed was introduced into a blastocyst even without sorting by using CD31 as an index, a high chimera forming ability was also observed. The chimera formation rates are shown in FIG. 2, (A).

This result revealed that the chimera forming ability of a primed pluripotent stem cell is improved by the forced expression of E-cadherin. Since the chimera forming ability is considered to be lost when the cell is further differentiated, it is presumed that the primed pluripotent stem cell is put in a less differentiated state by the forced expression of E-cadherin.

Furthermore, the gene expression profile of the primed pluripotent stem cell in which E-cadherin was forcedly expressed was analyzed.

From the CD31 positive cell (CD31(+)) and the CD31 negative cell (CD31(−)) obtained by the forced expression of E-cadherin, mRNAs are respectively extracted by a usual method to synthesize cDNAs. Thereafter, Taqman Mouse Stem Cell Pluripotency Array (manufactured by Life Technologies Corporation) was used in accordance with the manufacturer's manual to compare gene expression patterns of these cells.

As a result, it was found that the expression of genes known as markers for a naive pluripotent stem cell such as Rex1 and Pecam1 was higher in the CD31 positive cell (CD31(+)) obtained by the forced expression of E-cadherin (see FIG. 2, (B)). Besides, it was found that the expression of a gene known as a marker for a primed pluripotent stem cell such as T was lower (see FIG. 2, (B)).

This revealed that a primed pluripotent stem cell is converted to a naive pluripotent stem cell (namely, the reversion is caused) by the forced expression of E-cadherin.

Example 3: Improvement of Reversion Efficiency by Combination of Forced Expression of E-Cadherin and Activation of STAT3 Signal This example demonstrates that the reversion efficiency is remarkably improved by activating a STAT3 signal in addition to the forced expression of E-cadherin.

The activation of a STAT3 signal was carried out by stimulating the cell with LIF.

As for EB3DR-EpiSC, a doxycycline-dependent E-cadherin induced cell was obtained in the same manner as in Example 2-1 (which cell will be hereinafter referred to as the EB3DR-EpiSC-TRE-Cdh1).

The EB3DR-EpiSC-TRE-Cdh1 was cultured for 7 days in the presence of a basic fibroblast growth factor (bFGF) or LIF in a usual medium (Dox(−)) or a medium supplemented with 10 μg/mL of doxycycline (Dox(+)), and the resultant cell was dissociated with a trypsin/EDTA solution and stained with an APC labeled anti-mouse CD31 antibody to be analyzed by using the FACS.

Figure 3:
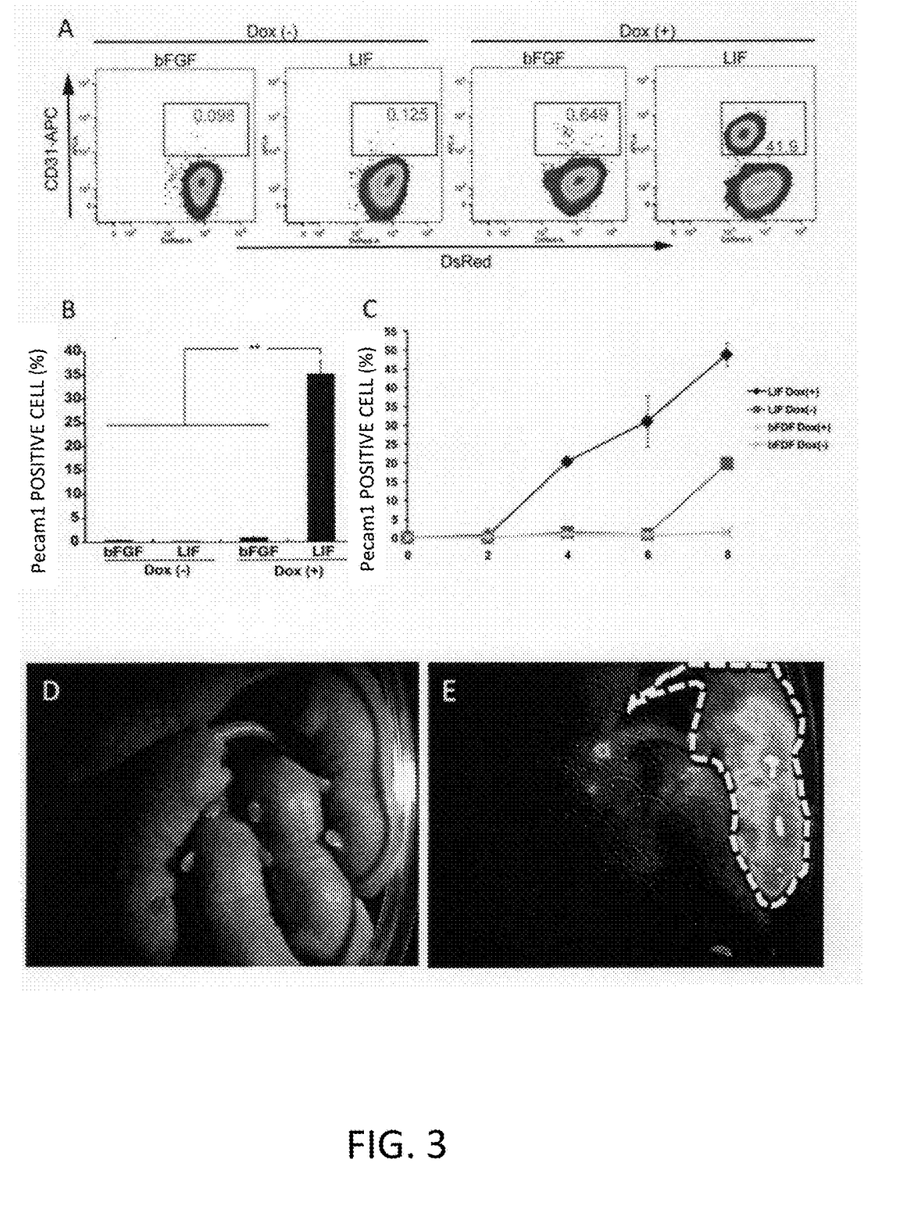

As a result, in the EB3DR-EpiSC-TRE-Cdh1, a CD31 (Pecam1) positive cell was observed at a high proportion merely when both the LIF stimulation and the forced expression of E-cadherin were employed in combination (see FIGS. 3, (A) and (B)). Although the expression of CD31 was induced also in a medium containing bFGF, the level was merely restrictive. Besides, when the time-dependent appearance change of the CD31 (Pecam1) positive cell was checked, it was found, as illustrated in FIG. 3, (C), that a cell expressing CD31 (Pecam1) appeared merely in 4 days if both the LIF stimulation and the forced expression of E-cadherin were employed in combination.

In the same manner as described in Example 2-2, the CD31 positive cell was sorted from the EB3DR-EpiSC-TRE-Cdh1 in which E-cadherin was forcedly expressed and which was stimulated with LIF, so as to check the chimera forming ability. Thus, it was revealed, as illustrated in FIG. 3, (E), that the EB3DR-EpiSC had attained a chimera forming ability because the fluorescence of DsRed derived from the EB3DR-EpiSC-TRE-Cdh1 was observed. Individuals in which particularly strong fluorescence was observed are surrounded with a dotted line in the drawing (see FIG. 3, (E)).

In this manner, it was found that if a STAT3 signal is activated in addition to the forced expression of E-cadherin, a primed pluripotent stem cell is dramatically improved in the chimera forming ability.

Example 4: Inhibition of Wnt/β Catenin Signal and Reversion of Pluripotent Stem Cell In this example, IWP-2 and XAV939 were used as a Wnt/β catenin signal inhibitor to confirm their effects on the reversion.

First, in order to confirm the effect of IWP-2 on a Wnt/β catenin signal inhibition, the amount of protein in β catenin was checked by Western blotting. The EB3DR-EpiSC was cultured under the aforementioned culturing conditions, IWP-2 (at a final concentration of 5 nM) was added thereto, and the resultant was cultured for another 2 days. As a control, the same amount of DMSO was added instead of IWP-2. Next, Nuclear/Cytosol Fractionation Kit (Bio Vision, manufactured by Mountain View, Calif.) was used in accordance with the manufacturer's manual to separate a cytoplasmic fraction and a nuclear fraction. Each of these fractions thus obtained was dissolved in Laemmli Sample Buffer (Bio-Rad, manufactured by Hercules, Calif.) to perform SDS-PAGE. A protein separated by the SDS-PAGE was blotted on a PVDF transfer membrane (manufactured by Millipore Corporation) to perform a primary antibody reaction.

As a primary antibody, an anti-β catenin antibody (#9562, 1:1000), an anti-(β-actin antibody (#3770, 1:1000), or an anti-histone H3 antibody (#4499, 1:2000) purchased from Cell Signaling Technology Inc. was used. As a secondary antibody, for the anti-β catenin antibody or the anti-histone H3 antibody, an anti-rabbit IgG Horseradish peroxidase-conjugated antibody (NA934V, 1:100, manufactured by GE Healthcare UK, Little Chalfont, UK) was used for the reaction, and for the anti-β-actin antibody, an anti-mouse IgG Horseradish peroxidase-conjugated antibody (NA931V, 1:1000, manufactured by GE Healthcare UK, Little Chalfont, UK) was used for the reaction, and then a band bonded to the secondary antibody was detected by SuperSignal West Pico Chemiluminescent Substrate (manufactured by Thermo Fisher Scientific Inc., Rockford, Ill.). As a result, it was confirmed that the amount of β catenin was reduced in the nuclear fraction by IWP-2 and that a Wnt/β catenin signal was thus inhibited (see FIG. 4, (A)).

The EB3DR-EpiSC was cultured in N2B27 medium (Ying et al., Nature (2008), 435, 519-523) supplemented with 1,000 U/mL of mouse LIF and 1 μM of PD0325901 (manufactured by Axon, Groeningen, The Netherlands). To the resultant, 5 nM of IWP-2 (manufactured by Wako Pure Chemical Industries, Ltd., Osaka, Japan) was added, or CHIR known as an inhibitor of GSK3β or the same amount of DMSO was added instead of IWP-2, so as to check the influence on the EB3DR-EpiSC.

Figure 4:
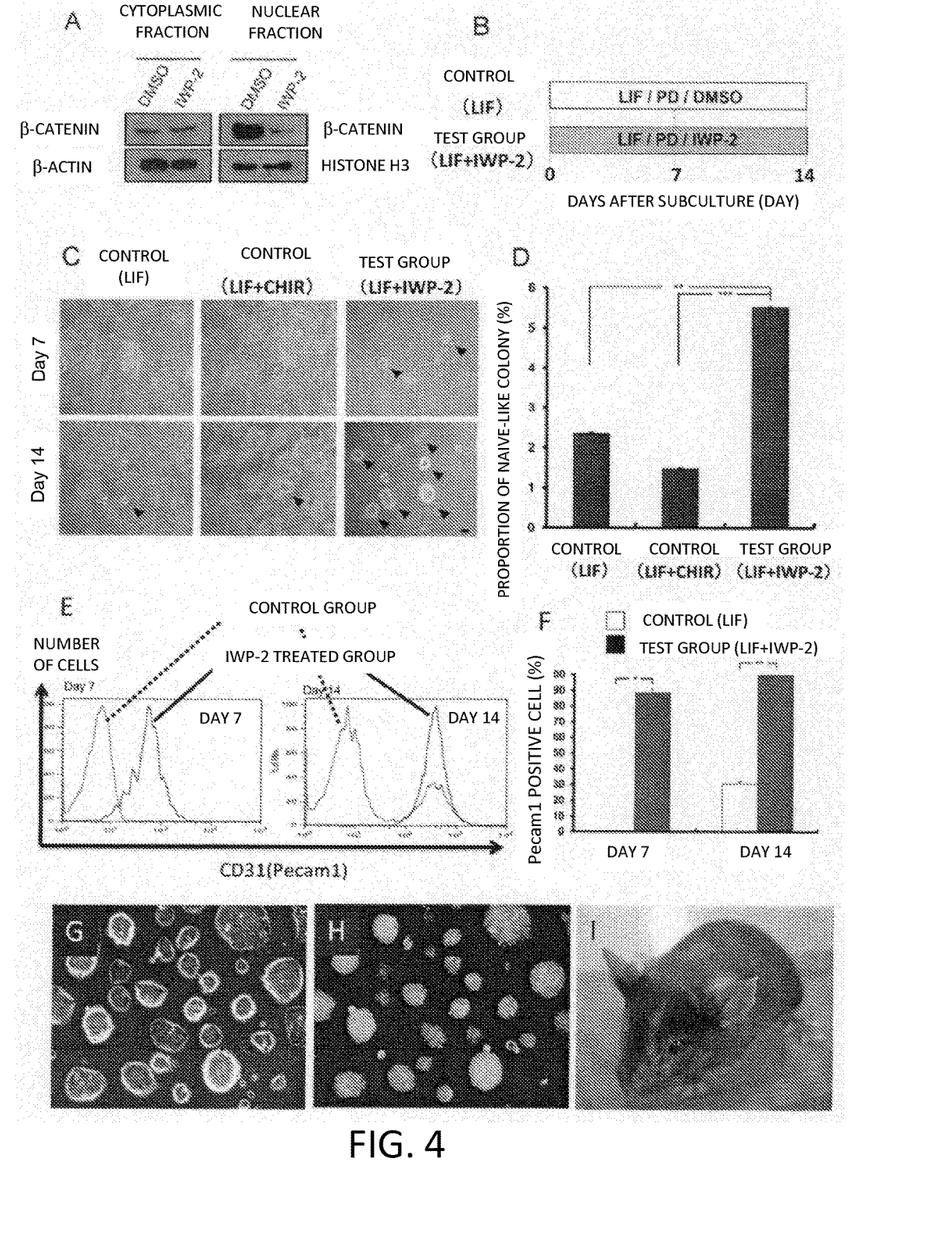

As a result, under the condition where IWP-2 was added, the appearance of a colony corresponding to a naive pluripotent stem cell-like morphology was observed within 7 days after culture, and the colony appearance frequency was increased on the 14th day after culture (see FIG. 4, (C)). Besides, the appearance frequency of a colony characteristic to the naive pluripotent stem cell on the 14th day after culture (shown with an arrow head in FIG. 4, (C)) was significantly increased by adding IWP-2 (see FIGS. 4, (C) and (D)). Furthermore, when the cell was subcultured thereafter for a long period of time, it could be cultured while keeping this morphology (data not shown). This revealed that the EpiSC was converted to a naive pluripotent stem cell by the treatment with LIF and IWP-2.

Next, the expression of CD31 (PECAM-1) in these cells was analyzed. The expression level of CD31 was checked by the FACS by using an APC labeled rat anti-mouse CD31 antibody (manufactured by eBioscience, 17-0311). As a result, it was found that CD31 is expressed at a high frequency in a short period of time in the presence of LIF and IWP-2 (see FIGS. 4, (E) and (F)). When a colony of the CD31 expressing cell was cloned and subcultured, a mouse ES cell-like morphology was obtained (see FIG. 4, (G)), and such a cell could be subcultured continuously for a long period of time similarly to a mouse ES cell. Since the cell was derived from the EB3DR-EpiSC, DsRed was expressed therein (see FIG. 4, (H)).

Furthermore, the chimera forming ability of the EB3DR-EpiSC treated with LIF and IWP-2 was checked. Specifically, the embryo of a BDF1 (C57BL6/N; DBA1 F1) mouse was cultured in Medium 2 (manufactured by Millipore Corporation) to the eight-cell stage or morula stage. The resultant embryo was transferred to KSOM medium (manufactured by Millipore Corporation) and cultured for 24 hours to be developed to the blastocyst stage. For the injection into an embryo, the cell was dissociated into a single cell by a trypsin treatment, and the resultant was suspended in a medium. A zona pellucida was perforated under a microscope by using a piezoelectric micromanipulator, and a chimeric embryo was produced by injecting approximately 10 cells into a space below the zona pellucida in each embryo. After the injection, the embryo was cultured in KSOM medium until a blastomere was obtained, and then, the resultant was transplanted into the uterus of a pseudopregnant ICR recipient female mouse. The chimera formation was checked on the basis of the color of a fur. A cell derived from BDF1×C57BL/6 grows a black fur, and a cell derived from 129/Ola grows a brown (agouti-colored) fur. The color of the fur of a born mouse was found to be a chimeric color of black and brown, and the obtained mouse was confirmed, based on the fur color, as a chimeric mouse (see FIG. 4, (I)). Specifically, it was revealed that the EpiSC treated with IWP-2 was improved in its chimera forming ability and had been converted to a naive pluripotent stem cell capable of producing a chimeric animal.

Besides, the cell reversion was confirmed by using another Wnt/β catenin signal inhibitor.

The naive-like colony formation and the chimera formation were checked in the same manner as described above except that XAV939 (manufactured by Sigma-Aldrich, S. Louis, Mo., USA) was used as the Wnt/β catenin signal inhibitor instead of IWP-2.

Figure 5:
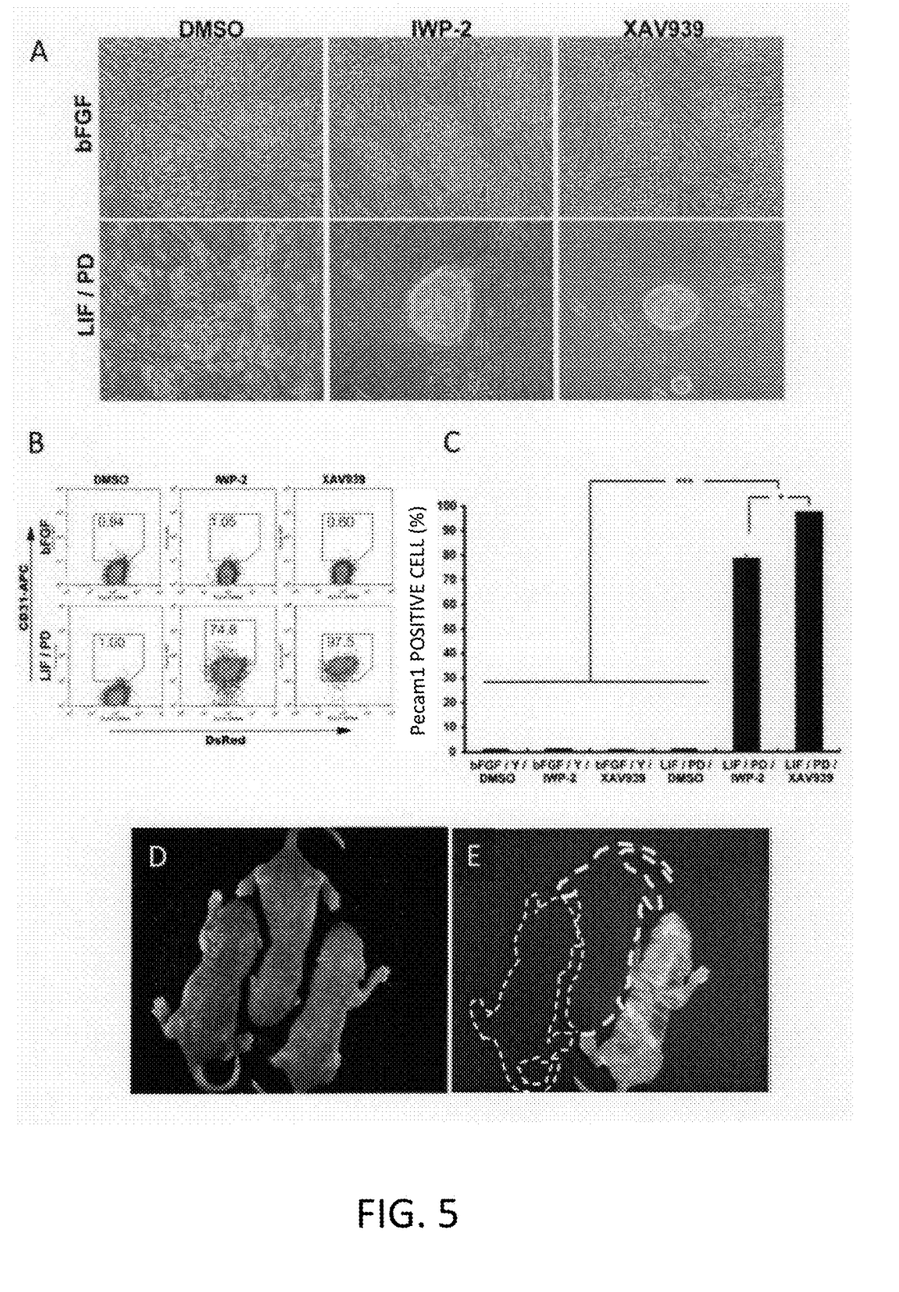
FIG. 5 illustrates effects of treatment with a combination of LIF and IWP-2 or XAV939, in which (A) is a diagram illustrating that an EpiSC treated with a combination of LIF and IWP-2 or XAV939 forms a naive-like colony, (B) is a diagram of expression of CD31 (Pecam-1), (C) is a graph of a proportion of a CD31 (Pecam-1) positive cell, and (D) and (E) are photographs illustrating that the EpiSC treated with the combination of LIF and IWP-2 or XAV939 makes a contribution to chimerism.

Also in using XAV939 as the Wnt/β catenin signal inhibitor, a cell formed a naive-like colony on the $7^{th}$ day after treatment when LIF was used in combination, which is similar to the result obtained by using IWP-2 (see FIG. 5, (A)). Besides, with respect to the expression of CD31, also in using XAV939 as the Wnt/β catenin signal inhibitor, a CD31 positive cell was observed at a high frequency, which is similar to the result obtained by using IWP-2 (see FIG. 5, (B)). Furthermore, with respect to the proportion of the CD1 (PECAM-1) positive cell on the $7^{th}$ day after treatment, when LIF was used in combination, the proportion of the CD1 (PECAM-1) positive cell was remarkably increased also in using XAV939 as the Wnt/β catenin signal inhibitor, similarly to the result obtained by using IWP-2 (see FIG. 5, (C)). Moreover, with respect to the production of a chimeric animal, also in using the XAV939 as the Wnt/β catenin signal inhibitor, a chimeric animal was produced similarly to the result obtained by using IWP-2 (see FIG. 5, (E)).

Example 5: Gene Expression Profile of Converted Cell

The gene expression profile of the primed pluripotent stem cell (wit-rESC) in which the Wnt/β catenin signal was inhibited and the STAT3 signal was activated in Example 4 was checked.

The gene expression profile was obtained in the same manner as described in Example 2-2. As a comparative control, a mouse ES cell (ESC), an E-cadherin forcedly expressing cell (E-cad rESC) obtained in Example 2 and an EpiSC were used.

Figure 6:
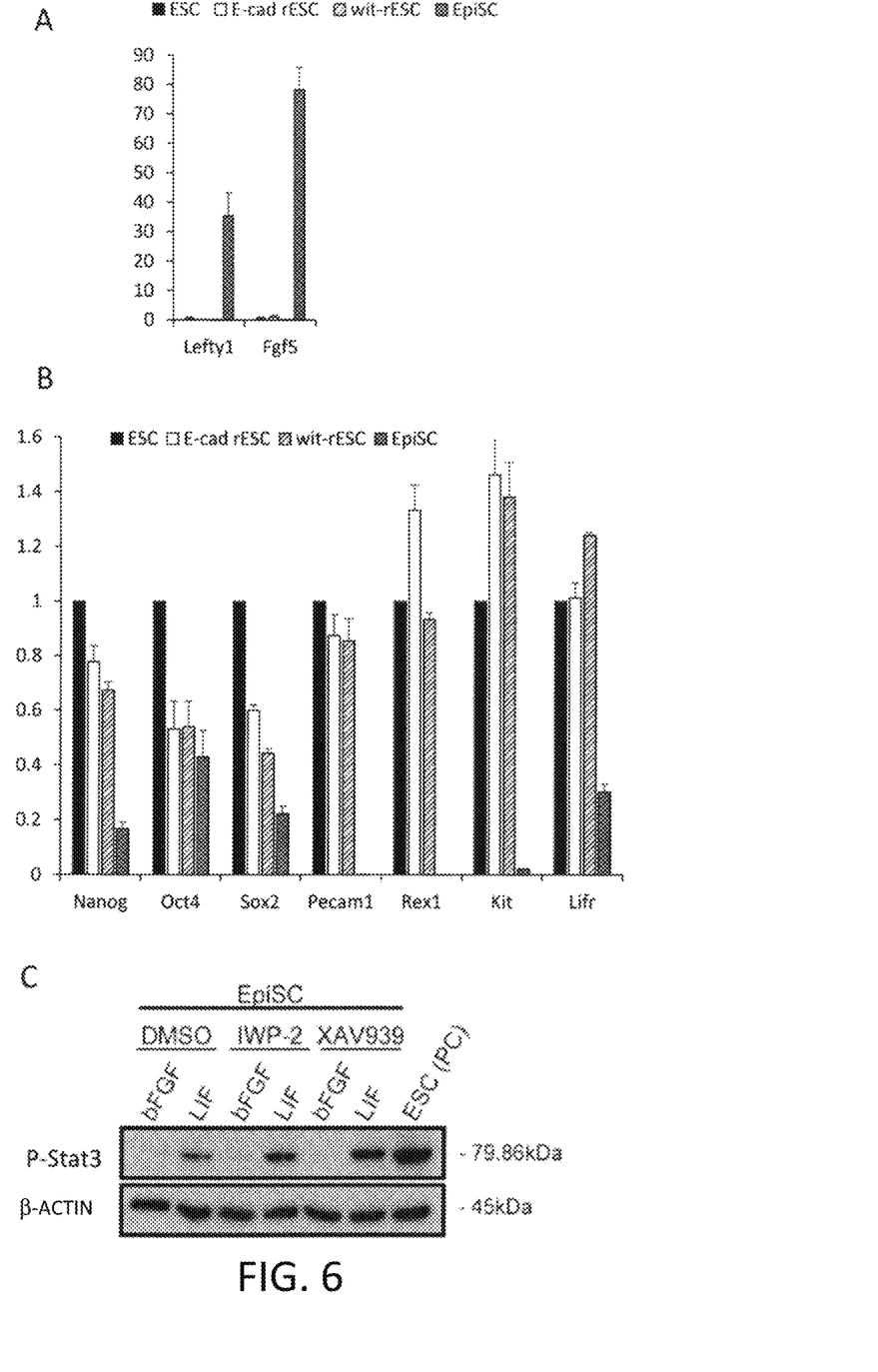
FIG. 6 illustrates expression levels of stem cell markers and activation of a STAT3 signal, in which (A) is a diagram illustrating the expression levels of primed pluripotent stem cell markers, (B) is a diagram illustrating the expression levels of naive pluripotent stem cell markers, and (C) is a diagram for confirming activation of a STAT3 signal, in which "ESC" indicates an embryonic stem cell, "E-cad rESC" indicates an EpiSC in which E-cadherin is forcedly expressed, and "wit-rESC" indicates an EpiSC in which a Wnt/β catenin signal is inhibited and a STAT3 signal is activated.

When the expression of Lefty1 and Fgf5, which are known as markers for a primed pluripotent stem cell, was checked, their expression levels were lowered in the CD31 positive pluripotent stem cells (wit-rESC and E-cad rESC) obtained in Examples 2 and 4 to an equivalent level to that in the ES cell (see FIG. 6, (A)).

When the expression of Rex1, Pecam1, Kit and the like, which are known as markers for a naive pluripotent stem cell, was checked, their expression levels were increased in the pluripotent stem cells (wit-rESC and E-cad rESC) obtained in Examples 2 and 4 to an equivalent level to that in the ES cell (see FIG. 6, (B)).

It is understood from these results that a primed pluripotent stem cell subjected to the Wnt/β catenin signal inhibition and the STAT3 activation has been converted to a naive pluripotent stem cell also in terms of the gene expression profile. It is also understood that a primed pluripotent stem cell subjected to the E-cadherin forced expression and the STAT3 activation has been converted to a naive pluripotent stem cell.

Besides, the EB3DR-EpiSC was stimulated with LIF, the resultant cell was collected on the 2nd day after stimulation, and the activation of a STAT3 signal was checked by the Western blotting. The activation of a STAT3 signal was checked on the basis of the presence of phosphorylated STAT3. The phosphorylated STAT3 was detected by using, as a primary antibody, an anti-P-STAT3 antibody (#9145, 1:2000, manufactured by Cell Signaling Technology Inc.) (1:1000) specifically recognizing phosphorylated STAT3.

The activation of a STAT3 signal was not observed in the absence of LIF but the activation of a STAT3 signal was definitely observed in the presence of LIF (see FIG. 6, (C)). Besides, the activation of a STAT3 signal was also observed in the presence of IWP-2 or XAV939 (see FIG. 6, (C)).

What is claimed is:

1. A method of increasing chimera forming ability of a primed pluripotent stem cell, comprising treating a primed pluripotent stem cell with a Wnt/β-catenin signal transduction selective inhibitor and a signal transducer and activator of transcription 3 (STAT3) activator to place the primed pluripotent stem cell in a state where a Wnt/β-catenin signal is selectively inhibited, among Wnt signaling pathways, and a STAT3 signal is activated, wherein following the treatment the primed pluripotent stem cell has increased chimera forming ability compared to an untreated control primed pluripotent stem cell.

2. A method for producing a chimeric non-human mammal, comprising introducing the pluripotent stem cell produced by the method according to claim 1 into a non-human mammalian blastocyst and developing the blastocyst to produce a chimeric non-human mammal.

3. The method according to claim 1, wherein the treating comprises treating the primed pluripotent stem cell with a β-catenin degradation accelerator and LIF.

4. The method according to claim 1, wherein the Wnt/β-catenin signal transduction selective inhibitor comprises XAV939.

* * * * *